United States Patent [19]
Delk et al.

[11] Patent Number: 5,641,325
[45] Date of Patent: Jun. 24, 1997

[54] ICE PACK

[75] Inventors: Robert E. Delk, Dallas; Michael L. Bowen, Arlington; Pervez Dagia, Dallas, all of Tex.

[73] Assignee: Tecnol, Inc., Fort Worth, Tex.

[21] Appl. No.: 314,848

[22] Filed: Sep. 29, 1994

Related U.S. Application Data

[63] Continuation-in-part of Ser. No. 294,142, Aug. 22, 1994, which is a continuation-in-part of Ser. No. 45,360, Apr. 13, 1993, Pat. No. 5,356,426.

[51] Int. Cl.$^6$ .................................................... A61F 7/00
[52] U.S. Cl. ........................ 607/108; 607/112; 607/114; 126/204; 383/501; 62/530
[58] Field of Search ........................... 383/901; 62/530; 604/332; 126/204; 607/108–112, 114; 215/12.1, 13.1

[56] References Cited

U.S. PATENT DOCUMENTS

| | | | |
|---|---|---|---|
| D. 195,185 | 5/1963 | Witz | D83/1 |
| D. 276,596 | 12/1984 | Kisha | D9/435 |
| D. 327,329 | 6/1992 | Hubbard et al. | D24/207 |

(List continued on next page.)

FOREIGN PATENT DOCUMENTS

| | | | |
|---|---|---|---|
| 1263581 | 12/1989 | Canada | A61F 7/08 |
| 2820366 | 11/1978 | Germany | A61F 7/04 |
| 2846349 | 5/1980 | Germany | A61F 7/04 |
| 474249 | 10/1937 | United Kingdom . | |
| 1227892 | 4/1971 | United Kingdom | A61F 7/04 |

OTHER PUBLICATIONS

Copies of photographs showing "Plastech" clip produced prior to filing date of present application.
Product news for Nurses, p. 19, dated 1975.
Product news for Nurses, p. 26, dated 1973.
Hollister Bag Clamp, Advertisement, 1 page (undated).

U.S. Patent Application No. 08/535,715 filed Sep. 28, 1995 entitled *Ice Pack Clip*.
U.S. Patent Application No. 08/559,469 filed Nov. 15, 1995 entitled *Hot or Cold Chemical Therapy Pack*.
U.S. Patent Application 08/403,295 filed Mar. 14, 1995 entitled *A Reusable Hot or Cold Chemical Therapy*.
U.S. Patent Application 08/294,142 filed Aug. 22, 1994 and titled *Ice Pack*.
Hollister Advertisement "Product News For Nurses" Nursing, Date Unknown, p. 19.
Hollister Advertisement "Produce news For Nurses" Nursing, Date Unknown, p. 26.
Hollister, Bag Clamp, Undated, one page.
Hydro–Med Products, Inc. "Spectrum® thermal Bag With Extremity Band" Brochure, Date Unknown, one page.
BodyGlove® "Neoprene Ice Pack Wrap" Brochure, Date Unknown, one page.
Page from Unknown Catalog advertising among other things BodyGlove® Ice Pack Wraps, Date Unknown, one page.
Page from Unknown Catalog advertising among other things Thera–Med, Inc. Cold Packs, Date Unknown, one page.

(List continued on next page.)

*Primary Examiner*—Angela D. Sykes
*Assistant Examiner*—Robert L. Nasser, Jr.
*Attorney, Agent, or Firm*—Baker & Botts, L.L.P.

[57] ABSTRACT

An ice pack having a bag, securement devices, and a clip. The bag has two multi-layer walls which are bonded to form a containment section, a neck, a mouth, and a clip mounting tab. The layers of the bag walls perform various functions for the ice pack. The securement devices have hook strips mounted to the bag and pile straps attached to the bag. The pile straps wrap around the object to which the ice pack is to be applied, and engage the hook strips. The clip includes two plates connected together by a hinge. The elongated hooks are positioned such that the two elongated hooks engage when the plates are rotated about the hinge, and secure the neck of the bag between the two elongated hooks. The inner surfaces of the clip are attached to the clip mounting tab located near the neck of the bag, thereby facilitating the sealing of the bag by the clip.

8 Claims, 6 Drawing Sheets

U.S. PATENT DOCUMENTS

| | | | |
|---|---|---|---|
| 381,265 | 4/1888 | Martens . | |
| 785,638 | 3/1905 | Scritchfield . | |
| 858,550 | 7/1907 | Whall . | |
| 907,875 | 12/1908 | Pritchard . | |
| 1,169,123 | 1/1916 | Burns . | |
| 1,317,102 | 9/1919 | Reid | 383/901 |
| 1,459,735 | 6/1923 | Kraft . | |
| 1,549,510 | 8/1925 | Schnitzler . | |
| 1,819,913 | 8/1931 | Miller et al. . | |
| 1,964,655 | 6/1934 | Williamson | 128/258 |
| 2,043,327 | 6/1936 | Miller | 153/52 |
| 2,435,743 | 2/1948 | Geimer | 229/53 |
| 2,547,886 | 4/1951 | Poux | 62/1 |
| 2,589,577 | 3/1952 | Rosenthal et al. | 62/1 |
| 2,773,531 | 12/1956 | Johnson | 150/2.1 |
| 2,898,744 | 8/1959 | Robbins | 62/4 |
| 3,036,506 | 5/1962 | Andresen, Jr. | 95/11 |
| 3,092,110 | 6/1963 | Duensing | 128/293 |
| 3,171,184 | 3/1965 | Posse | 24/248 |
| 3,186,404 | 6/1965 | Gardner | 128/87 |
| 3,191,392 | 6/1965 | Donnelly | 62/4 |
| 3,247,852 | 4/1966 | Schneider | 128/346 |
| 3,306,288 | 2/1967 | Rosenfield | 128/157 |
| 3,356,086 | 12/1967 | Behney | 128/24 |
| 3,409,008 | 11/1968 | Mortensen et al. | 128/156 |
| 3,429,315 | 2/1969 | McDonald | 128/402 |
| 3,491,761 | 1/1970 | Baker | 128/402 |
| 3,523,534 | 8/1970 | Nolan | 128/283 |
| 3,551,965 | 1/1971 | Gordon | 24/248 |
| 3,607,521 | 9/1971 | Suominen et al. | 156/199 |
| 3,608,709 | 9/1971 | Pike | 206/47 |
| 3,610,307 | 10/1971 | Huff et al. | 150/2.1 |
| 3,621,539 | 11/1971 | Ayers | 24/30.5 |
| 3,669,115 | 6/1972 | Melges | 128/305 |
| 3,735,765 | 5/1973 | Ichelson | 128/335 |
| 3,736,769 | 6/1973 | Petersen | 62/530 |
| 3,749,620 | 7/1973 | Montgomery | 156/73 |
| 3,763,622 | 10/1973 | Stanley, Jr. | 53/25 |
| 3,818,553 | 6/1974 | Parmenter | 24/30.5 |
| 3,847,279 | 11/1974 | Montgomery | 206/219 |
| 3,856,008 | 12/1974 | Fowler et al. | 128/165 |
| 3,874,042 | 4/1975 | Eddleman et al. | 24/255 |
| 3,882,873 | 5/1975 | Arango | 128/379 |
| 3,885,403 | 5/1975 | Spencer | 62/530 |
| 3,893,834 | 7/1975 | Armstrong | 62/4 |
| 3,950,158 | 4/1976 | Gossett | 62/4 |
| 4,000,996 | 1/1977 | Jordan | 62/4 |
| 4,033,354 | 7/1977 | De Rosa | 128/379 |
| 4,038,726 | 8/1977 | Takabayashi | 24/198 |
| 4,044,773 | 8/1977 | Baldwin, III | 128/402 |
| 4,077,390 | 3/1978 | Stanley et al. | 126/263 |
| 4,081,150 | 3/1978 | Tyson | 128/402 |
| 4,081,256 | 3/1978 | Donnelly | 64/4 |
| 4,149,541 | 4/1979 | Gammons et al. | 128/400 |
| 4,190,054 | 2/1980 | Brennan | 128/402 |
| 4,204,543 | 5/1980 | Henderson | 128/402 |
| 4,212,303 | 7/1980 | Nolan | 128/346 |
| 4,222,422 | 9/1980 | Löfberg | 150/1 |
| 4,275,485 | 6/1981 | Hutchison | 24/30.5 |
| 4,294,582 | 10/1981 | Naslund | 23/230 |
| 4,296,529 | 10/1981 | Brown | 24/30.5 |
| 4,326,533 | 4/1982 | Henderson | 128/402 |
| 4,347,848 | 9/1982 | Hubbard et al. | 128/402 |
| 4,372,318 | 2/1983 | Viesturs et al. | 128/403 |
| 4,385,950 | 5/1983 | Hubbard et al. | 156/73.1 |
| 4,397,315 | 8/1983 | Patel | 128/403 |
| 4,402,402 | 9/1983 | Pike | 206/219 |
| 4,427,010 | 1/1984 | Marx | 128/402 |
| 4,462,224 | 7/1984 | Dunshee | 62/530 |
| 4,523,353 | 6/1985 | Hubbard et al. | 24/30.5 |
| 4,527,566 | 7/1985 | Abare | 128/402 |
| 4,537,184 | 8/1985 | Williams | 128/90 |
| 4,551,888 | 11/1985 | Beecher | 20/30.5 |
| 4,585,003 | 4/1986 | Meistrell | 128/402 |
| 4,586,506 | 5/1986 | Nangle | 128/403 |
| 4,628,932 | 12/1986 | Tampa | 128/402 |
| 4,688,572 | 8/1987 | Hubbard et al. | 128/402 |
| 4,751,119 | 6/1988 | Yukawa | 428/35 |
| 4,756,299 | 7/1988 | Podella | 607/114 |
| 4,780,117 | 10/1988 | Lahey | 62/4 |
| 4,805,620 | 2/1989 | Meistrell | 128/402 |
| 4,834,730 | 5/1989 | Holtermann et al. | 604/335 |
| 4,856,651 | 8/1989 | Francis | 206/219 |
| 4,887,335 | 12/1989 | Folkmar | 24/30.5 |
| 4,926,526 | 5/1990 | Brown et al. | 24/30.5 R |
| 4,931,333 | 6/1990 | Henry | 428/76 |
| 4,951,666 | 8/1990 | Inman et al. | 128/402 |
| 4,972,832 | 11/1990 | Trapini et al. | 128/402 |
| 4,981,135 | 1/1991 | Hardy | 607/108 |
| 4,983,172 | 1/1991 | Steer et al. | 604/332 |
| 4,986,076 | 1/1991 | Kirk et al. | 62/4 |
| 5,020,711 | 6/1991 | Kelley | 224/222 |
| 5,038,779 | 8/1991 | Barry et al. | 128/402 |
| 5,045,041 | 9/1991 | Murphy | 493/194 |
| 5,050,272 | 9/1991 | Robinson et al. | 24/30.5 |
| 5,052,387 | 10/1991 | Natali | 128/402 |
| 5,072,875 | 12/1991 | Zacoi | 128/400 |
| 5,074,300 | 12/1991 | Murphy | 128/402 |
| 5,109,841 | 5/1992 | Hubbard et al. | 128/380 |
| 5,125,133 | 6/1992 | Morrison | 24/30.5 |
| 5,133,348 | 7/1992 | Mayn | 383/901 |
| 5,152,034 | 10/1992 | Konings et al. | 24/30.5 R |
| 5,163,504 | 11/1992 | Resnick | 165/47 |
| 5,178,139 | 1/1993 | Angelillo | 128/403 |
| 5,184,470 | 2/1993 | Moser et al. | 62/4 |
| 5,205,278 | 4/1993 | Wang | 126/263 |
| 5,243,974 | 9/1993 | Allen | 607/108 |
| 5,261,241 | 11/1993 | Kitahara et al. | 62/4 |
| 5,275,156 | 1/1994 | Milligan | 607/114 |
| 5,277,695 | 1/1994 | Johnson, jr. et al. | 602/14 |
| 5,300,105 | 4/1994 | Owens | 607/114 |
| 5,356,426 | 10/1994 | Delk et al. | 607/112 |
| 5,379,489 | 1/1995 | Delk et al. | 24/30.5 |
| 5,409,500 | 4/1995 | Dyrek | 607/112 |
| 5,466,251 | 12/1995 | Brunson | 607/112 |

OTHER PUBLICATIONS

Tecnol "Jumbo Plus Ice Pack" Brochure, Date Unknown, one page.

Tecnol "Cold Therapy Products" Brochure, Date Unknown, one page.

Xerox of Package containing Tecnol Jumbo Plus Ice Pack, Date Unknown, one page.

Hollister, Inc., "Drain Clamp" Brochure, Date Unknown, one page.

Hollister, Inc., "The Protector for Draining Wounds" advertisement, *Nursing*, Feb., 1975, one page.

Hollister "Draining–Wound Management System" advertisement, *Nursing*, Date Unknown, one page.

Hollister, Inc. "Brief Urostomy Bag" advertisement, *Nursing*, Apr., 1973, one page.

ICE PACK

This application is a continuation-in-part of application Ser. No. 08/294,142, filed Aug. 22, 1994, pending, which is a continuation-in-part of application Ser. No. 08/045,360, filed Apr. 13, 1993, now U.S. Pat. No. 5,356,426.

BACKGROUND OF THE INVENTION

1. Field of the Invention

The present invention relates to ice packs, and more particularly to ice packs with a bag, a closure component, and components for securing the ice pack.

2. Description of the Related Art

Ice packs are used for cooling various surfaces such as cooling a portion of a patient's body for medical reasons. Ice packs generally have a bag with a containment section, a neck, and a mouth. Ice is inserted into the containment section of the bag through the mouth and neck of the bag. Once ice is inserted into the containment section of the bag, a closure component seals the containment section of the bag and the ice pack is applied to the desired location.

Ice in the containment section of the bag reduces the temperature of the bag for the intended use of the ice pack. However, temperature gradients can exist across the surface of the bag due to the concentration of ice in different areas in the containment section of the bag. Also, it would be an advantage to control the rate at which heat is transferred at the surface of the bag, and to control the temperature of the outer surface of the bag. Therefore, it would be an advantage to provide an ice pack with a bag that can reduce temperature gradients across the surface of the bag, help control the rate of heat exchange at the surface of the bag, and help control the temperature of the outer surface of the bag.

Once the ice has been inserted into the containment section of the bag, it is preferred that the containment section be closed off so that the ice and liquid in the containment section will not run out of the ice pack. Some of the closure components in used prior art ice packs to close off the containment section of a bag include such items as stoppers, clips, etc.

Generally, stoppers block the opening in neck of the bag, thereby preventing ice and liquids from escaping from the containment section of the bag. However, stoppers require a bag with a neck specifically designed for use with the stopper.

In contrast, clips do not require the neck portion of a bag to be specifically designed for use with the clip. A clip closes off the containment section of a bag by applying force to the external surfaces of the neck. The forces on the external surfaces of the neck force together the internal surfaces of the neck, thereby closing off the containment section of the bag.

Because the clip is a separate component from the bag of an ice pack, it is desirous to attach the clip to the bag. Attaching the clip to the bag prevents the loss of the clip, and searching to find a clip each time a ice pack is used. Typically, the clip will be attached to the bag at the location on the neck which the clip is intended to engage and seal.

However, various types of prior art clips, and the method of attaching those clips, are such that it is possible to close the clip without securing and sealing the neck of the ice bag. Therefore, there is a need for an ice pack having a clip which will facilitate closing the clip with the neck of the bag engaged in, and sealed by, the clip.

After the bag of the ice pack has been filled with ice and closed off by a closure component, the ice pack is applied to the desired surface. In prior art ice packs, tie strings have been attached to the bag in a longitudinal direction. The tie strings are wrapped around the object on which the ice pack is applied, and a knot is tied in the tie strings to secure the ice pack thereon.

However, it is difficult for a user to tie a knot in the tie strings when the user is applying the ice pack to the user's own body. Also, it is difficult to adjust the firmness with which the tie strings secure the ice pack to the applied area. Therefore, there is a need for an ice pack which can be easily attached and adjusted on the object being cooled.

SUMMARY

In one embodiment, the present invention is an ice pack which includes a bag having a first side wall welded to a second side wall to form a containment section, a neck, and a mouth. In one aspect, a first side wall includes a waterproof layer disposed in the area of the first side wall which forms the containment section, the neck, and the mouth, and includes an insulation layer disposed over the waterproof layer and in the area of the first side wall which forms the containment section of the bag. In a further aspect, a second side wall includes: a throat piece disposed in the area of the second side wall which forms the mouth, the neck, and an upper portion of the containment section; an insulation layer disposed over the throat piece and in the area of the second side wall which forms the containment section; and a waterproof layer disposed over the insulation layer and in the area of the second side wall which forms the containment section and an upper portion of the neck. In another further aspect, a second wall includes a waterproof layer disposed in the area of the second side wall which forms the containment section, the neck, and the mouth, and includes a relief layer disposed over the waterproof layer and in the area of the second side wall which forms the containment section. In another aspect, the side walls have an insulation layer disposed inside of a waterproof layer. In another aspect, the side walls have a throat element disposed in the area of the walls which form the neck and an upper portion of the containment section, an insulation layer disposed in the area of the walls which forms the containment section, and a waterproof layer disposed in the area of the walls which form the containment section and a lower portion of the neck. In a further aspect, the insulation layer in one of the walls is perforated with a plurality of holes. In yet a further aspect, the insulation layer in both walls is perforated with a plurality of holes. In yet a further aspect, the holes in the insulation layer of one of the walls is larger than the holes in the insulation layer of the other wall. In another further aspect, the insulation layer of one of the walls has more holes per square area than the insulation layer of the other wall. In another aspect, each of the walls includes a barrier layer which is disposed over the waterproof layer and in the area of the walls which forms the containment section and the neck section. In another aspect, the bag includes a mouth having a first handle which is formed in one of the side walls, and a second handle which is formed in the other side wall.

In another embodiment, the present invention includes a bag having a containment section, a neck, a mouth, and a clip. The clip has a first plate connected to a second plate by a hinge so that an inner surface of the first plate rotates toward an inner surface of the second plate. The clip also has a first elongated hook and a second elongated hook extending from the inner surfaces of the first plate and the second plate, respectively, so that the first elongated hook engages and secures with the second elongated hook when the inner surfaces of the first plate and the second plate are rotated towards each other. The neck of the bag is secured between the engaged first and second elongated hooks, thereby sealing the bag. In a further aspect, the clip is attached to the bag of the ice pack. In yet a further aspect, the inside surface of the first plate of the clip is attached to the neck of the bag.

In another embodiment, the present invention includes a bag having a containment section, a neck, a clip mounting tab, and a clip for securing the neck of the bag closed. The clip is attached to the clip mounting tab of the bag. In a further aspect, the bag has a clip mounting tab which is attached to the clip. In yet a further aspect, the clip mounting tab is mounted to the inside surface of the first plate of the clip.

In another embodiment, the present invention includes a bag having a first securement device. The first securement device has a first means for engaging mounted on the bag, a strap attached to the bag, and a second means for engaging mounted on the strap. The second means for engaging is adapted to engage with and secure to the first means for engaging. In a further aspect, the present invention includes a second securement device having a first means for engaging mounted to the bag, a strap attached to the bag, and second means for engaging mounted to the strap and adapted to engage and secure with the first means for attaching of the second securement device. In yet a further aspect of the invention, the first means for attaching and the second means for attaching of the first securement device are components of a hook and pile type fastener. In yet a further aspect of the present invention, the first means for attaching and the second means for attaching of the second securement device are components of a hook and pile type fastener.

BRIEF DESCRIPTION OF DRAWINGS

For a more complete understanding of the present invention, and for further objectives and advantages thereof, reference may now be taken in conjunction with the accompanying drawings herein.

DETAILED DESCRIPTION

Figure 1:
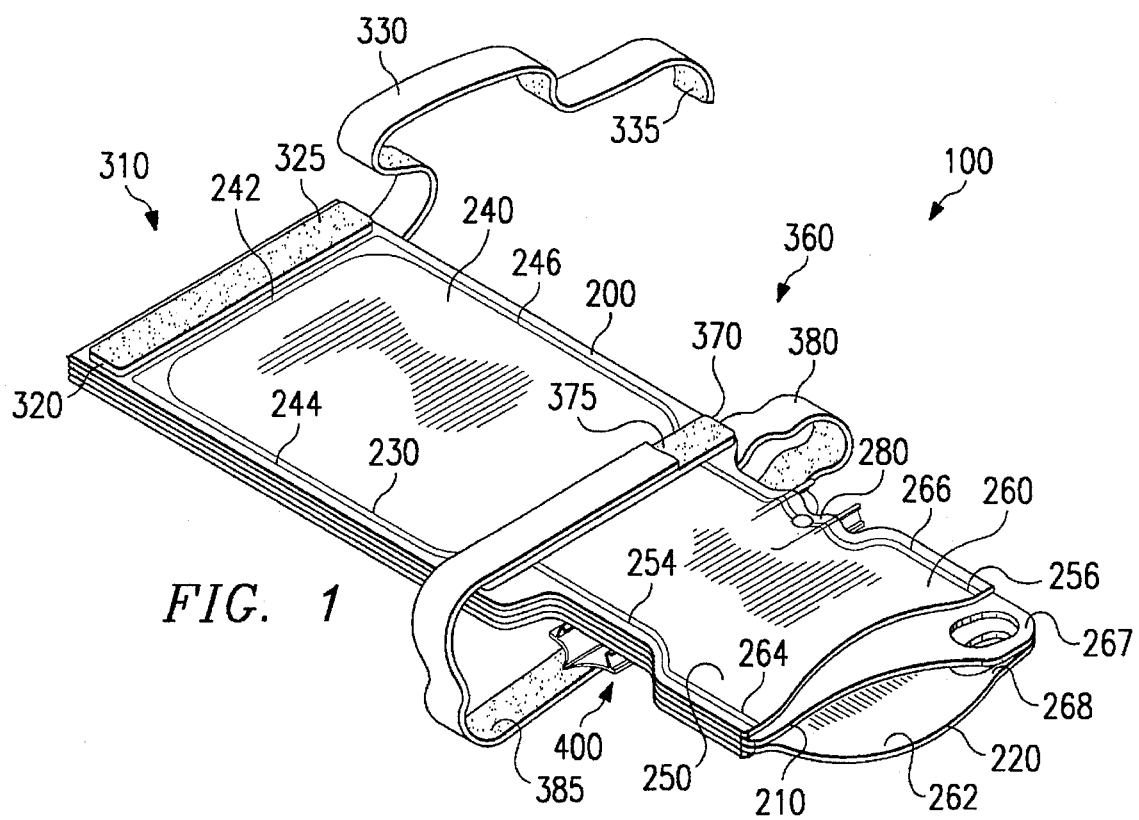
FIG. 1 is a perspective view of an embodiment of the present invention illustrated as an ice pack.

Referring first to FIG. 1, there is shown a perspective view of an embodiment of the present invention, illustrated as an ice pack 100. The ice pack 100 generally comprises a bag 200, securement devices 310 and 360, and a clip 400.

Still referring to FIG. 1, the bag 200 has a first side wall 210 and a second side wall 220 joined together by a weld 230 to form a containment section 240, a neck 250, a mouth 260, and a clip mounting tab 280. As illustrated, the containment section 240 is a generally rectangular shape with a bottom 242, a first side 244, and a second side 246. However, the containment section 240 can be alternative shapes such as oval or any other shape which can contain the ice and liquids therein. The neck 250 has a first side 254 and a second side 256 which extend from the sides 244 and 246, respectively, of the containment section 240 to the mouth 260 of the bag 200. The first and second side 254 and 256 form a passage or throat in the inside of the neck 250 which communicates with the interior of the containment section 240. The mouth 260 has a first side 264 and a second side 266 which extend from the first and second side 254 and 256 of the neck 250, respectively, to an opening 262. The opening 262 of the mouth 260 communicates with the interior or throat of the neck 250. The mouth 260 of the bag 200 also has a first handle 267 and a second handle 268 disposed on the walls 210 and 220, respectively, in the area of the opening 262. The clip mounting tab 280 is preferably located adjacent to the neck 250. Although the mouth 260 has been illustrated herein as larger than the neck 250, in another construction the mouth 260 can be the same size or smaller than the neck 250. Furthermore, although the containment section 240 has been illustrated herein as larger than the neck 250, in yet another construction the containment section 240 can be the same size or smaller than the neck 250.

Figure 2:
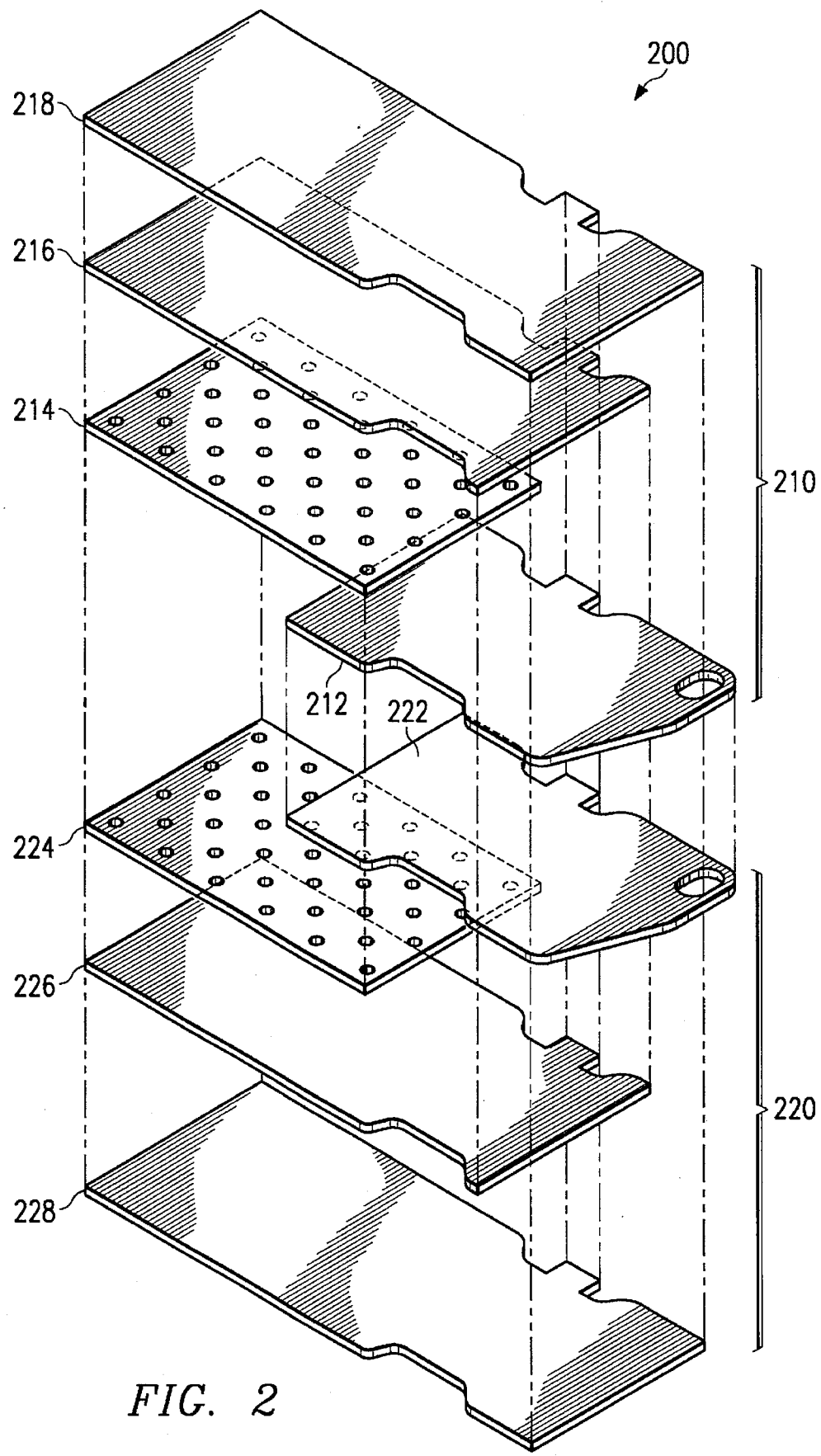
FIG. 2 is an exploded perspective view of an embodiment of the bag from FIG. 1.

Referring now to FIG. 2, there is illustrated an exploded perspective view of an embodiment of the bag 200 from FIG. 1. The containment section 240, the neck 250, and the mouth 260 of the bag 200 in FIG. 1 are formed by joining the first side wall 210 to the second wall 220 with the weld 230 in FIG. 1. The first side wall 210 is a multilayered material having a throat element 212, a first layer or insulation layer 214, a waterproof layer 216, and an outer barrier layer 218. Likewise, the second wall 220 has a throat element 222, a first layer or insulation layer 224, an waterproof layer 226, and an outer barrier layer 228.

Still referring to FIG. 2, the throat elements 212 and 222 are disposed in the area of the walls 210 and 220, respectively, which form the neck 250 and the mouth 260 of the bag 200 in FIG. 1. The throat elements 212 and 222, also cover a portion of the walls 210 and 220, respectively, in an upper portion of the containment section 240 of the bag 200 in FIG. 1. Also, handles 267 and 268 are formed on the throat elements 212 and 222, respectively. The throat elements 212 and 222 are preferably formed of polyethylene or other waterproof material. However, because the throat elements 212 and 222 do not contact the ice and liquids for an extended period of time, it is not necessary that the throat elements 212 and 222 be formed of a waterproof material.

Referring still to FIG. 2, the insulation layers 214 and 224 are disposed over the throat elements 212 and 222, respectively, in the area of the walls 210 and 220 which form the containment section 240 of the bag 200 in FIG. 1. The insulation layers 214 and 224 control the heat transfer rate and temperature of the walls 210 and 200. The insulation layers 214 and 224 are preferably formed of a foam or other insulation material. In the illustrated embodiment of the invention, the insulation layers 214 and 224 are a closed cell foam perforated with holes. The size and density of the holes in the insulation layers are selected to provide a specific heat transfer rate and select temperature for the walls 210 and 220. Preferably, the size and density of holes in the insulation layer 214 are different from the size and density of the holes in the insulation layer 224, thereby causing the first side wall 210 to have a different heat transfer rate and temperature than the second side wall 220. In another construction, only one of the insulation layers 214 and 224 of the walls 210 and 220, respectively, is perforated with holes. The absence of holes in the insulation layer of one of the walls 210 or 220 will cause the wall without holes to transfer heat at a slower rate and have a higher temperature than the other wall. In another construction, the insulation layer 214 of the first side wall 210 is a different thickness than the insulation layer 224 of the second side wall 220, thereby causing the first side wall 210 to have a different heat transfer rate and temperature than the second side wall 220. In yet another construction, the insulation layer 214 of the first side wall has a different thermal conductivity than the insulation layer 224 of the second side wall 220, thereby causing the first side wall 210 to have a different heat transfer rate and temperature than the second side wall 220.

Still referring to FIG. 2, the waterproof layers 216 and 226 are disposed over the insulation layers 214 and 224, respectively, in the area of the walls 210 and 220 which form the containment section 240 of the bag 200 in FIG. 1. The waterproof layers 216 and 226, also cover a portion of the walls 210 and 220, respectively, in a lower portion of the neck 250 of the bag 200 in FIG. 1. The waterproof layers 216 and 226 are preferably formed of polyethylene or other waterproof material.

Referring still to FIG. 2, it can be seen that in the area of the neck 250, the throat elements 212 and 222 overlap with the waterproof layers 216 and 226, respectively in the area of the walls 210 and 220 which form the neck 250. The throat elements 212 and 222 are sealed to the respective waterproof layers 216 and 226 in this overlapping area of the neck 250 by ultrasonic welding, chemical bonding, or the like. In this manner the throat elements 212 and 222 and the waterproof layers 216 and 226 will contain the ice and liquid inside the bag 200 of FIG. 1. In another construction, the waterproof layers 216 and 226 are disposed in an area of the walls 210 and 220, respectively, that covers a sufficient area of the neck 250 that the clip 400 (shown in FIG. 1) will seal the waterproof layers 216 and 226. In another construction, the throat element 212 and the waterproof layer 216 of the first side wall 210 are bonded to the insulation layer 214 of said first side wall 210 in the area which forms the neck 250, and the throat element 222 and the waterproof layer 226 of the second side wall 220 are bonded to the insulation layer 224 of the second side wall 220 in the area which forms the neck 250, thereby containing the ice and liquid inside the bag 200 of FIG. 1. In another construction, the insulation layer 214 of the First side wall 210 is bonded to the waterproof layer 216 of the first side wall, thereby regulating the space for ice and liquid to accumulate between the insulation layer 214 and the waterproof layer 216. In yet another construction, the insulation layer 224 of the second side wall 220 is bonded to the waterproof layer 226 of the second side wall 220, thereby regulating the space for ice and liquid to accumulate between the insulation layer 224 and the waterproof layer 226.

Still referring to FIG. 2, the barrier layers 218 and 228 are disposed over the waterproof layers 216 and 226, respectively, in the area of the walls 210 and 220 which form the containment section 240, the neck 250, and the mouth 260, excluding the handles 267 and 268. The barrier layers 218 and 228 reduce the amount of moist air contacting the waterproof layers, reduce the amount of any moisture which may condense on the waterproof layers from contacting the user, and provide a surface texture for the user which is more pleasant than the waterproof layers. The barrier layers 218 and 228 are preferably formed of a spun polyester material or the like.

Figure 3:
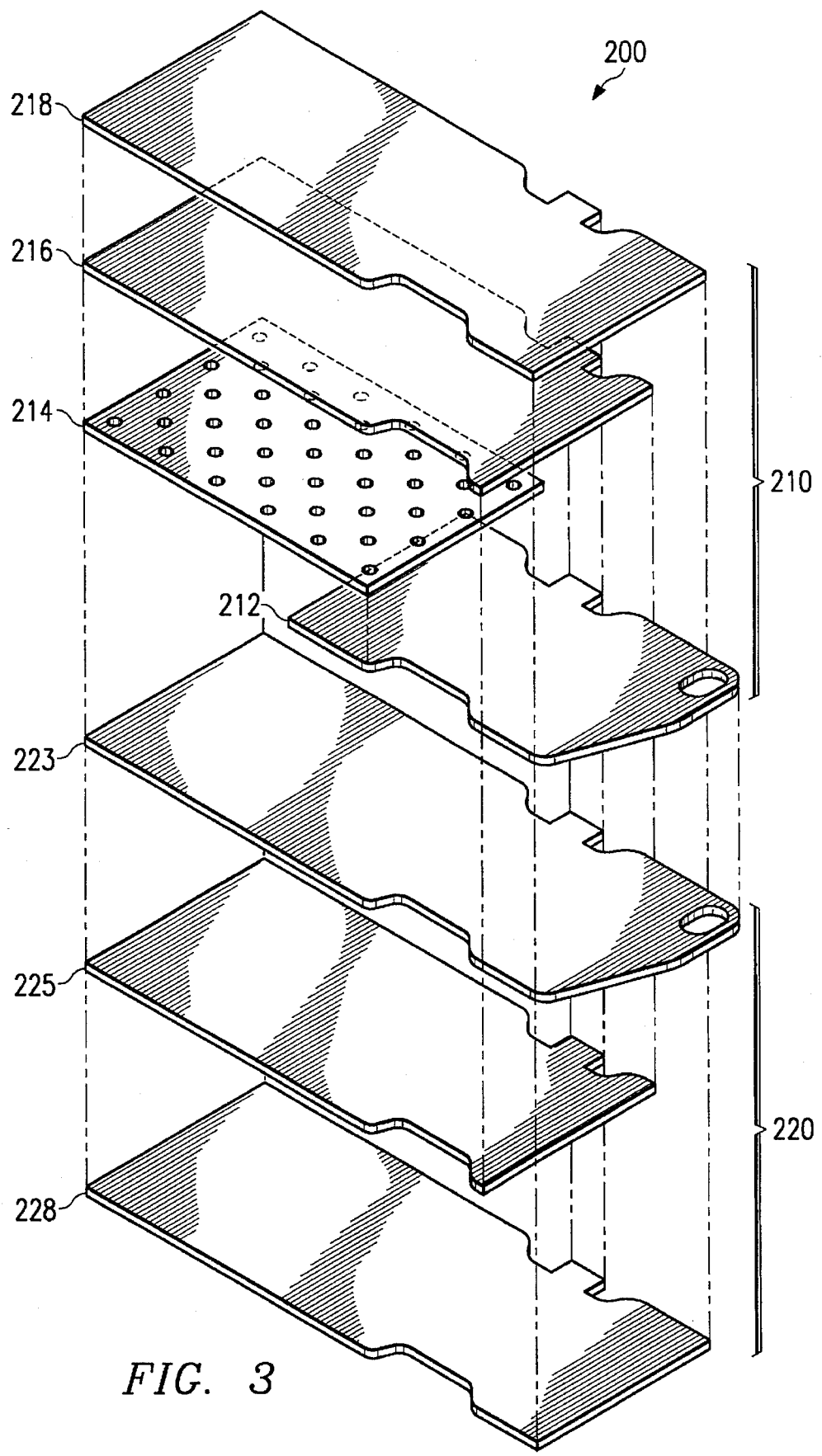
FIG. 3 is an exploded perspective view of an alternate embodiment of the bag from FIG. 1.

Referring now to FIG. 3, there is illustrated an exploded perspective view of another construction of the bag 200 from FIG. 1. The containment section 240, the neck 250, and the mouth 260 of the bag 200 in FIG. 1 are formed by joining the first side wall 210 to the second side wall 220 with the weld 230 in FIG. 1. As previously shown in reference to FIG. 2, the first side wall comprises the throat element 212, the first layer or insulation layer 214, the waterproof layer 216, and the barrier layer 218. However, the second side wall 220 comprises a waterproof layer 223, a relief layer 225, and the barrier layer 228.

Still referring to FIG. 3, the waterproof layer 223 is disposed in the area of the wall 220 which forms the containment section 240, the neck 250, and the mouth 260 of the bag 200 in FIG. 1. Also, handle 268 is formed on the waterproof layer 223 in the area of the opening 262 of the mouth 260 in FIG. 1 of the bag 200. The waterproof layer 223 is preferably formed of polyethylene or other waterproof material. In this manner, the waterproof layer 223 combined with the throat element 212 and the waterproof layer 216 will contain the ice and liquid inside the bag 200 of FIG. 1.

Referring still to FIG. 3, the relief layer 225 is disposed over the waterproof layer 213, and in the area of the wall 220 which forms the containment section 240 of the bag 200 in FIG. 1. The relief layer 225 also covers a portion of the wall 220 in a lower portion of the neck 250 of the bag 200 in FIG. 1. The relief layer 225 is preferably formed of polyethylene or other material. The relief layer 225 has a surface texture with many rises and recesses. The rises and recesses of the relief layer 225 reduce the amount of smooth flat surface. Smooth surfaces facilitate the formation and spread of condensation on a layer, while surfaces with relief or texture will retard the spread of condensation. Also, the rises and recesses of the relief layer 225 form air pockets which facilitate insulation of the side wall 220. The insulation provide by the relief layer 225 controls the heat transfer rate and temperature of the side wall 220. The insulation provided by the relief layer 225 also helps control the rate at which the side wall 220 initially reaches the desired temperature. By controlling the rate at which the side wall 220 reaches the desired temperature, condensation can be reduced which is caused by the side wall 220 reaching the desired temperature too quickly. The rises and recesses of the relief layer 225 can be formed by casting, embossing, or other like methods of forming rises and recesses in the relief layer 225. Alternatively, the relief layer 225 is formed of a material such as "bubble pack", having rises and recesses formed around pockets in the material.

Still referring to FIG. 3, the barrier layer 228 is disposed over the relief layer 225, and in the area of the wall 220 which forms the containment section 240, the neck 250, and the mouth 260, excluding the handle 268. The barrier layer 228 reduces the amount of moist air contacting the relief layer 225, reduces the amount of any moisture which may condense on the relief layer from contacting the user, and provides a surface texture for the user that is more pleasant that the relief layer 225.

Figure 7:
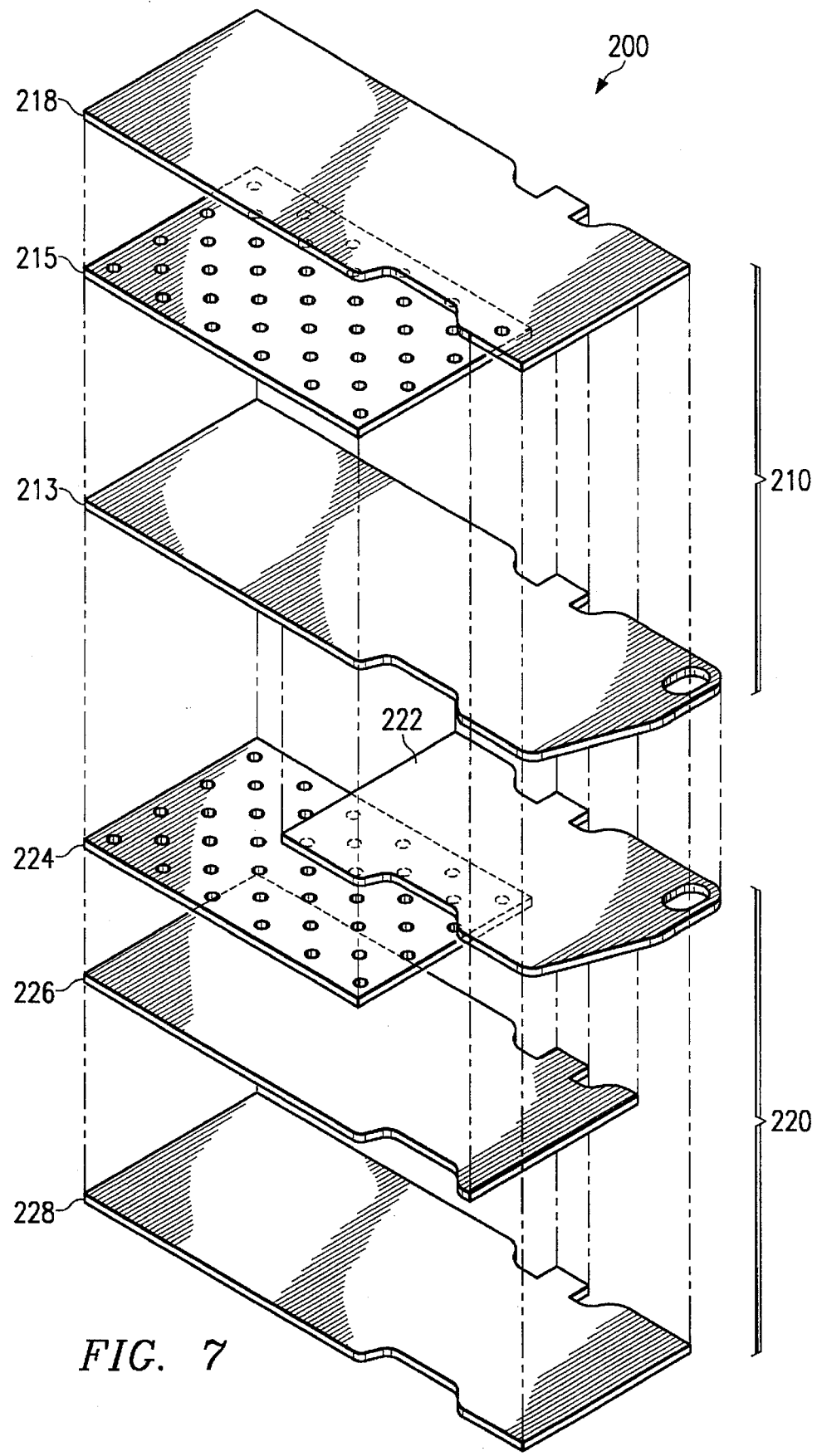
FIG. 7 is an exploded perspective view of an alternate embodiments of the bag from FIG. 1.

Referring now to FIG. 7, there is illustrated an exploded perspective view of another construction of the bag 200 from FIG. 1. The containment section 240, the neck 250, and the mouth 260 of the bag 200 in FIG. 1 are formed by joining the first side wall 210 to the second side wall 220 with the weld 230 in FIG. 1. The first side wall comprises a waterproof layer 213, an insulation layer 215, and the barrier layer 218. The second side wall 220 comprises the throat element 222, the first layer or insulation layer 224, the waterproof layer 226, and the barrier layer 228, as shown and described in reference to FIG. 2.

Still referring to FIG. 7, the waterproof layer 213 is disposed in the area of the wall 210 which forms the containment section 240, the neck 250, and the mouth 260 of the bag 200 in FIG. 1. Also, handle 267 is formed on the waterproof layer 213 in the area of the opening 262 of the mouth 260 in FIG. 1 of the bag 200. The waterproof layer 213 is preferably formed of polyethylene or other waterproof material. In this manner, the waterproof layer 213 of the first side wall 210 will act in combination with the throat element 222 and the waterproof layer 226 of the second side wall 220 to contain the ice and liquid inside the bag 200 of FIG. 1.

Referring still to FIG. 7, the insulation layer 215 is disposed over the waterproof layer 213 in the area of the wall 210 which forms the containment section 240 of the bag 200 in FIG. 1. The insulation layer 215 controls the heat transfer rate and temperature of the wall 210. The insulation layer 215 is preferably formed of a foam or other insulation material. The insulation layer 215 is preferably bonded to the waterproof layer 213 over the entire surface of the insulation layer 215; however, the insulation layer 215 can be bonded to the waterproof layer 213 in only select locations, such as the weld 230 in FIG. 1. In the illustrated embodiment of the invention, the insulation layer 234 is a closed cell foam perforated with holes. The size and density of the holes in the insulation layer 215 are selected to provide a specific heat transfer rate and select temperature for the wall 210. In another construction, the insulation layer 215 is a closed cell foam which is not perforated with holes. In yet another construction, the thickness of the insulation layer 215 is selected to provide a specific the heat transfer rate and temperature for the first side wall 210. In yet another construction, the thermal conductivity of the insulation layer 215 is selected to provide a specific the heat transfer rate and temperature for the first side wall 210. Preferably, the insulation layer 215 causes the first side wall 210 to have a different heat transfer rate and temperature than the second side wall 220.

Still referring to FIG. 7, the barrier layer 218 is disposed over the insulation layer 215, and in the area of the wall 210 which forms the containment section 240, the neck 250, and the mouth 260, excluding the handle 267. The barrier layer 218 reduces the amount of moist air contacting the insulation layer 215, reduces the amount of any moisture which may condense on the insulation layer 215 from contacting the user, and provides a surface texture for the user that is more pleasant that the insulation layer 215.

Figure 8:
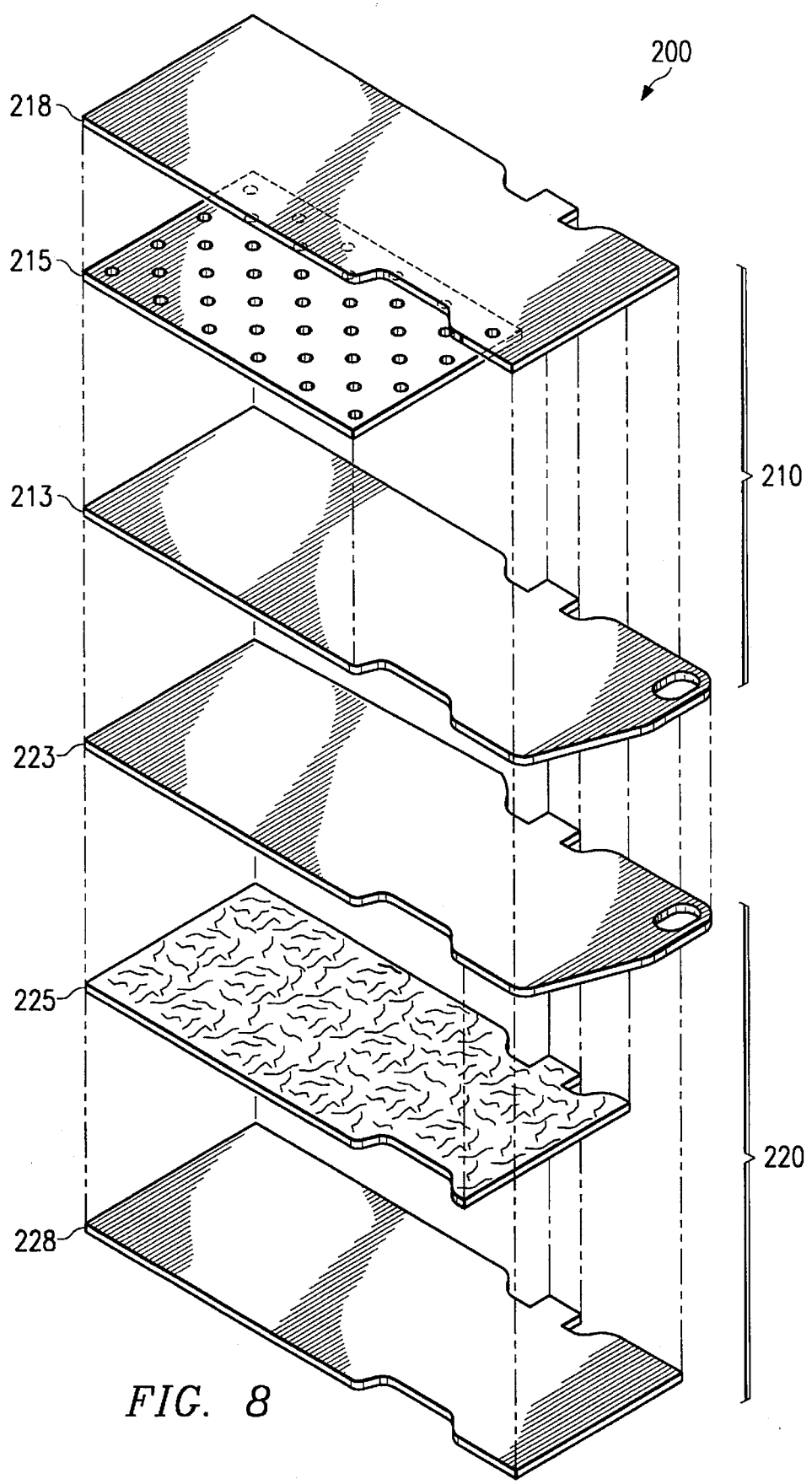
FIG. 8 is an exploded perspective view of an alternate embodiment of the bag from FIG. 1.

Referring now to FIG. 8, there is illustrated an exploded perspective view of another construction of the bag 200 from FIG. 1. The containment section 240, the neck 250, and the mouth 260 of the bag 200 in FIG. 1 are formed by joining the first side wall 210 to the second side wall 220 with the weld 230 in FIG. 1. The first side wall comprises the waterproof layer 213, the insulation layer 215, and the barrier layer 218, as shown and described in reference to FIG. 7. The second side wall 220 comprises the waterproof layer 223, the relief layer 225, and the barrier layer 228, as shown and described in reference to FIG. 3.

Referring now to FIGS. 1, 2, 3, 7, and 8 in combination, it can be seen how the bag 200 is formed. The layers of the walls 210 and 220 are positioned and trimmed to the desired shape of the bag 200. In the process of trimming the walls 210 and 220, a section of the material is left with the walls 210 and 220 near the throat 256 of the neck 250 for forming the clip mounting tab 280. The positioned and trimmed layers of the walls 210 and 220 are then bonded together by the weld 230. The weld 230 progresses around the walls 210 and 220 to form the containment section 240, the neck 250, and the mouth 260 of the bag 200. The weld 230 can be a sonic weld, heat weld, or bonding method, such as glue, or the like.

Still referring to FIGS. 1, 2, 3, 7 and 8 in combination, the layers of the walls 210 and 220 are bonded together in the area of the of the clip mounting tab 280 by sonic welding, heat welding, or chemical bonding, or the like. By bonding the layers of the walls 210 and 220 together, the clip mounting tab 280 presents a surface which facilitates mounting the clip 400 thereon. Although the clip mounting tab 280 has been illustrated as being an integral part of the walls 210 and 220, the clip mounting tab 280 could be a separate component which is mounted to the walls 210 and 220 of the bag 200. Furthermore, although the clip mounting tab 280 is illustrated as being positioned on the side of the neck 250, the clip mounting tab 280 could be located on any area of the bag 200.

Referring back now to FIG. 1, the securement devices 310 and 360 each include a hook strip 320 and 370, respectively, and a pile strap 330 and 380, respectively. The hook strips 320 and 370 have hook surfaces 325 and 375, respectively, which are a closely spaced apart multiplicity of hook-like members. The pile straps 330 and 380 have pile surfaces 335 and 385 with loose loops of filament fibers which are designed to cooperate with the hooks in the hook surfaces 325 and 375 in the hook strips 320 and 370, respectively. The hook surfaces 325 and 375 of the hook strips 320 and 370, respectively, engage the pile surfaces 335 and 385 of the hook strips 330 and 380, respectively, in the manner of the well known hook-and-pile fasteners.

Still referring back to FIG. 1, the hook strip 320 is mounted on the first wall 210 near the bottom 242 of the containment section 240, with the hook surface 325 facing away from the first wall 210. The pile strap 330 is mounted on the second wall 220 near the bottom 242 of the containment section 240, with the pile surface 335 facing away from the second wall 220. The pile strap 330 has a sufficient length to pass around an object that the ice pack 100 is to be applied, and engage the hook strip 320.

Referring back still to FIG. 1, the hook strip 370 is mounted on the first wall 210 near the intersection of the containment section 240 and the neck 250, with the hook surface 375 facing away from the wall 210. The pile strap 380 is mounted on the second wall 220 near the intersection of the containment section 240 and the neck 250, with the pile surface 385 facing away from the second wall 220. The pile strap 380 has a sufficient length to pass around an object that the ice pack 100 is to be applied, and engage the hook strip 370.

Still referring back to FIG. 1, although the securement device 310 has been illustrated with the hook strip 320 mounted to the first wall 210 and the pile strap 330 mounted to the second wall 220, the hook strip 320 can be mounted to the second wall 220 and the pile strap 330 mounted to the first wall 210, or both the hook strip 320 and the pile strap 330 can be mounted to the same wall of the bag 200. Similarly, the hook strip 370 can be mounted to the second wall 220 and the pile strap 330 mounted to the first wall 210, or both the hook strip 370 and the pile strap 330 can be mounted to the same wall of the bag 200. Also, although the securement devices 310 and 360 have been illustrated as members of a hook and pile fastener, any other similar engaging means can be used such as buttons, snaps, or the like.

Figure 4:
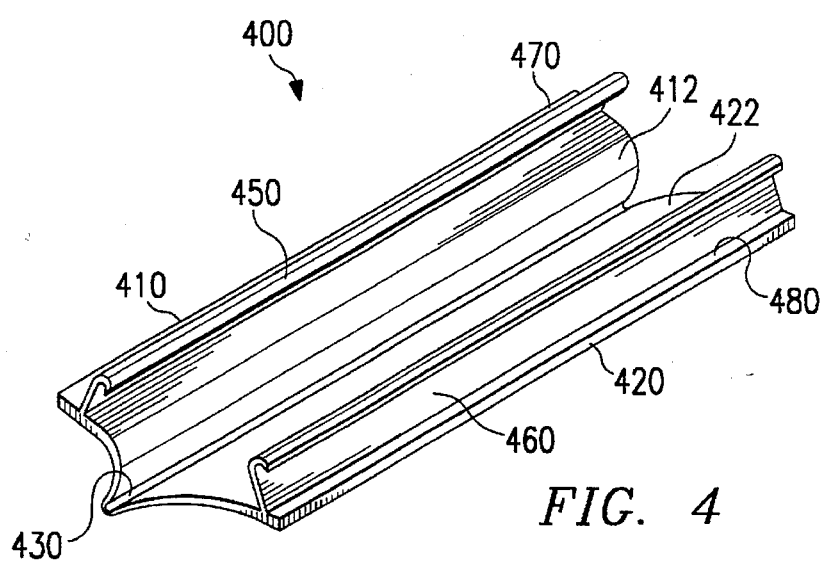
FIG. 4 is a perspective view of an embodiment of the clip from FIG. 1.

Referring now to FIG. 4, there is shown a perspective view of an embodiment of the clip 400 from FIG. 1. The clip 400 generally comprises a first plate 410 pivotally connected to a second plate 420 by a hinge 430. The clip 400 can be formed of a resilient plastic, or the like. The first plate 410 and the second plate 420 have an inner surface 412 and an inner surface 422, respectively. The first plate 410 and the second plate 420 are connected to the hinge 430 such that the inner surface 412 of the first plate 410 rotates to face the inner surface 422 of the second plate 420.

Referring still to FIG. 4, an elongated hook 450 extends outwardly from the inner surface 412 of the first plate 410. Likewise, an elongated hook 460 extends outwardly from the inner surface 422 of the second plate 420. The elongated hook 450 and the elongated hook 460 are positioned on the first plate 410 and the second plate 420, respectively, such that when the first plate 410 and the second plate 420 are rotated towards each other about the hinge 430, the elongated hook 450 and the elongated hook 460 engage. The elongated hooks 450 and 460 can also be located on the first plate 410 and the second plate 420, respectively, such that grip portions 470 and 480 of the first plate 410 and the second plate 420, respectively, provide sufficient area for a user to grasp the handles 470 and 480 for opening the clip 400.

Referring now to FIG. 1 and FIG. 4 in combination, it can be seen how the clip 400 attaches to the bag 200. The clip mounting tab 280 of the bag 200 is positioned on the inner surfaces 412 and 422 of the clip 400 so that the neck 250 of the bag 200 is centered within the clip 400. After positioning the clip 400, the clip 400 is attached to the clip mounting tab 280 of the bag 200 by sonic welding, hot glue, bonding, an adhesive strip, a fastener, or the like. Although the ice pack 100 has been illustrated with the clip 400 attached to the clip mounting tab 280 of the bag 200, the clip 400 could also be attached directly to any portion of the walls 210 and 220 in the area of the neck 250. Furthermore, although the bag 200 is illustrated as being attached to the inner surfaces 412 and 422 of the clip 400, the bag 200 could be attached to any area of the clip 400. In another construction, the clip 400 could be attached to the bag 200 by tape or a similar means for attaching.

Figure 5:
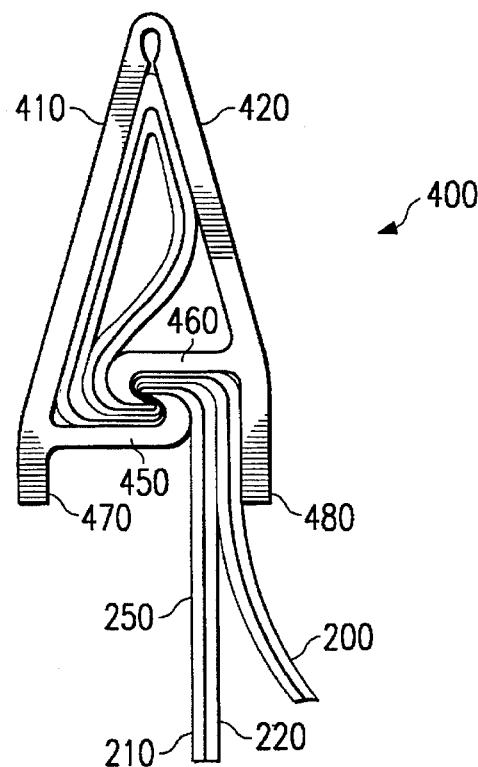
FIG. 5 is a partial side view of the ice pack from FIG. 1, illustrating the bag from FIG. 1 being closed by the clip from FIG. 4.

Referring now to FIG. 5, there is shown a partial side view of the ice pack 100 from FIG. 1, illustrating the bag 200 being closed by the clip 400. As illustrated, the first plate 410 and the second plate 420 of the clip 400 are rotated to a position where the elongated hooks 450 and 460 are engaged. The walls 210 and 220 of the bag 200 are folded over in the area of the neck 250 and are positioned between the elongated hooks 450 and 460 of the clip 400. The force of the elongated hooks 450 and 460 engaging each other will apply a force to the exterior of the walls 210 and 220 of the bag 200, which will force the interior surfaces of the walls 210 and 220 together and prevent ice and liquids in the containment section 240 of the bag 200, in FIG. 1, from escaping through the neck 250 and the mouth 260 of the bag 200.

Figure 6:
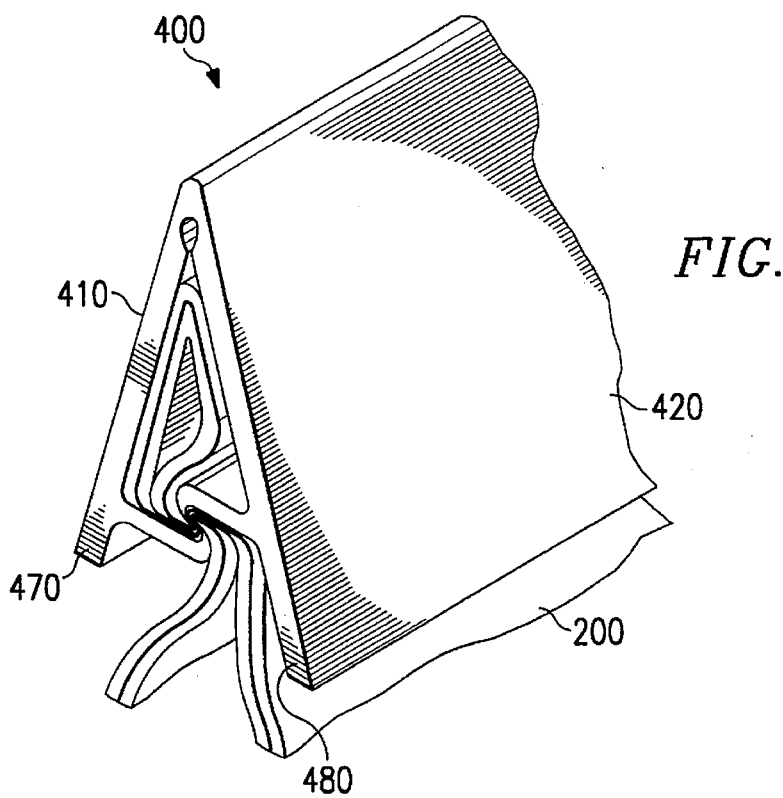
FIG. 6 is a partial perspective view of the ice pack from FIG. 1, illustrating the bag from FIG. 1 being closed by the clip from FIG. 4.

Referring now to FIG. 6, there is shown a partial perspective view of the ice pack 100 from FIG. 1, illustrating the bag 200 being closed by the clip 400. As illustrated, the first plate 410 and the second plate 420 of the clip 400 are contoured at a first end 470 and a second end 480 of the clip 400. The contour of the first plate 410 and the second plate 420 is such that sharp corners are reduced at the first end 470 and the second end 480 of the clip 400 when the clip 400 is in the closed position. The reduction of sharp corners on the clip 400 prevents injury to the user.

Referring now to FIGS. 1–8 in combination, it can be seen how the ice pack 100 of the present invention is utilized. Ice is inserted into the bag 200 through the opening 262 in the mouth 260 of the bag 200. The throat elements 212 and 222 extend below the insulation layers 214 and 222 into the containment section 240 of the bag 200, thereby allowing ice and liquids pass into the containment section 240 of the bag 200 without obstruction by the insulation layers 214 and 224. After sufficient ice is placed within the containment section 240 of the bag 200, any air in the containment section 240 can be kneaded out through the opening 262 in the mouth 260 of the bag 200.

Still referring to FIGS. 1–8 in combination, the neck 250 of the bag 200 is positioned completely within the clip 400 by gently pressing the neck 250 of the bag 200 in between the elongated hooks 450 and 460 of the clip 400. Once the neck 250 of the bag 200 is positioned within the clip 400, the first plate 410 and the second plate 420 are rotated about the hinge 430 until the elongated hooks 450 and 460 engage, thereby securing the neck 250 of the bag 200 therebetween. In this manner, the clip 400 will secure the layers of the ice pack together at the neck 250 and prevent the escape of ice and liquids within the containment section 240 of the bag 200. However, if the neck 250 of the bag 200 is not positioned completely within the clip 400, the user will be alerted to the improper interface by the difficulty of closing the clip 400, or the obscure angle of the clip 400 relative to the neck 250 of the bag 200.

Referring still to FIGS. 1–8 in combination, the containment portion 240 of the bag 200 containing the ice can be placed against the location which is desired to cool. The user can apply either the first side wall 210 of the bag 200 against the surface to be cooled, or the second side wall 220 of the bag 200 against the surface to be cooled, depending on the degree of heat transfer and temperature difference which is desired by the user. Liquids inserted into the bag 200 with the ice, or from the melting of the ice, will pass through the holes perforated in the insulation layers 214 and 224 of the walls 210 and 220. A pocket of liquid will form in between the insulation layer 214 and the waterproof layer 216 of the first wall 210, and in between the insulation layer 224 and the waterproof layer 226 of the second wall 220. These pockets of liquid facilitate the transfer of heat and reduce temperature gradients, or hot and cold "spots" across the surface of the first side wall 210 or the second side wall 220.

Still referring to FIGS. 1–8 in combination, the ice pack 100 is secured to an object by wrapping the pile straps 330 and 380 around the object and fastening the pile straps 330 and 380 to the first side hook strips 320 and 370, respectively. Because the pile straps 330 and 380 fasten to the hook strips 320 and 370 simply by applying a slight pressure, the user will be able to secure the ice pack 100 with only one free hand. In contrast, the prior art devices are secured by tying a knot in a pair of straps, which requires the use of both hands. Therefore, a user will need assistance from another person to secure the prior art device ice pack to an area of the body such as an arm. The improvement of securement devices 310 and 360 will allow a user to apply and adjust the ice pack 100 on an area, such as an arm, without assistance from another person.

Referring still to FIGS. 1–8 in combination, once the user is finished with using the ice pack 100, the ice pack 100 can be opened by pulling the mouth 240 of the bag 200 away from the containment section 240 of the bag 200. This will force the elongated hooks 450 and 460 of the clip 400 to separate, and allow the neck 250 of the bag 200 to open. After the bag 200 has been opened, the ice and liquids can be removed from the ice pack 100 through the opening 262 in the mouth 260 of the bag 200, and the ice pack 100 can be discarded or saved for later use.

Although the present invention has been described in considerable detail with reference to certain preferred embodiments thereof, other embodiments are possible. For example, the multilayered bag described herein can be used without a clip, or with any type of clip, or without the clip mounting tab. As another example, the clip mounting tab described herein can be used with any type of bag or with any type of clip. As yet another example, the clip described herein can be used with any type of bag, or without the clip mounting tab. As yet another example, the securement devices described herein can be used with any type of bag and without the clip. Therefore, the spirit and scope of the appended claims should not be limited to the description of the preferred embodiments contained herein.

What is claimed is:

1. An ice pack bag having a containment section, a neck, and a mouth, said ice pack bag further comprising:

a first side wall including:

a waterproof layer disposed in the area of the first side wall which forms said containment section, said neck, and said mouth; and an insulation layer disposed over the waterproof layer and in the area of the first side which forms the containment section; and a second side wall;

wherein said first side wall is welded to said second side wall to form said containment section, said neck being in communication with said containment section, and said mouth being in communication with said neck and having an opening; and wherein said second side wall further includes:

a throat piece disposed in the area of said second side wall which forms the mouth, the neck, and an upper portion of the containment section;

an insulation layer disposed over the throat piece and in the area of said second side wall which forms the containment section; and a waterproof layer disposed over the insulation layer and in the area of said second side wall which forms the containment section, the neck, and an upper portion of the neck.

2. The ice pack bag according to claim 1, wherein the insulation layer of said second side wall is bonded to the waterproof layer of said second side wall.

3. The ice pack bag according to claim 1, wherein the insulation layer of said second side wall is provided with a plurality of holes.

4. The ice pack bag according to claim 1, wherein said second side wall includes a barrier layer disposed over the waterproof layer and in the area of said second side wall which forms the containment section of said bag.

5. The ice pack bag according to claim 1, wherein said first side wall includes a barrier layer disposed over the insulation layer and in the area of said first side wall which forms the containment section of said bag.

6. The ice pack bag according to claim 1, including a first handle formed in said first side wall adjacent to the opening in said mouth; and a second handle formed in said second side wall adjacent to the opening in said mouth.

7. The ice pack bag according to claim 6, wherein said first handle comprises a hole formed in the waterproof layer of said first side wall, and wherein said second handle comprises a hole formed in the waterproof layer of said second side wall.

8. An ice pack bag having a containment section, a neck, and a mouth, said ice pack bag further comprising:

a first side wall including:

a waterproof layer disposed in the area of the first side wall which forms said containment section, said neck, and said mouth; and an insulation layer disposed over the waterproof layer and in the area of the first side which forms the containment section; and a second side wall;

wherein said first side wall is welded to said second side wall to form said containment section, said neck being in communication with said containment section, and said mouth being in communication with said neck and having an opening;

wherein said second side wall further includes:

a throat piece disposed in the area of said second side wall which forms the mouth, the neck, and an upper portion of the containment section;

an insulation layer disposed over the throat piece and in the area of said second side wall which forms the containment section; and a waterproof layer disposed over the insulation layer and in the area of said second side wall which forms the containment section, the neck, and an upper portion of the neck; and wherein said second side wall has a different heat transfer rate than said first side wall.

* * * * *